United States Patent
Aubert et al.

(10) Patent No.: US 11,667,462 B2
(45) Date of Patent: *Jun. 6, 2023

(54) AEROSOL DEVICE WITH MULTI-APERTURE DIFFUSION FOR HAIR SHAPING AND/OR STYLE HOLDING

(71) Applicant: L'OREAL, Paris (FR)

(72) Inventors: Lionel Aubert, Asnieres sur Oise (FR); Jonathan Gawtrey, Boulogne (FR); Céférino Rodrigues, Montreuil (FR); Nadia Smail, Vernouillet (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/888,002

(22) PCT Filed: Apr. 30, 2014

(86) PCT No.: PCT/EP2014/058892
§ 371 (c)(1),
(2) Date: Oct. 29, 2015

(87) PCT Pub. No.: WO2014/177646
PCT Pub. Date: Nov. 6, 2014

(65) Prior Publication Data
US 2016/0075501 A1    Mar. 17, 2016

(30) Foreign Application Priority Data
Apr. 30, 2013   (FR) ........................ 1354013

(51) Int. Cl.
| | |
|---|---|
| B65D 83/30 | (2006.01) |
| A61Q 5/06 | (2006.01) |
| A61K 8/34 | (2006.01) |
| A61K 8/04 | (2006.01) |
| A61K 8/19 | (2006.01) |
| B65D 83/14 | (2006.01) |
| B65D 83/28 | (2006.01) |
| A45D 7/04 | (2006.01) |
| A61K 8/81 | (2006.01) |
| B65D 83/20 | (2006.01) |
| B05B 1/14 | (2006.01) |

(52) U.S. Cl.
CPC .............. *B65D 83/30* (2013.01); *A45D 7/04* (2013.01); *A61K 8/046* (2013.01); *A61K 8/19* (2013.01); *A61K 8/34* (2013.01); *A61K 8/817* (2013.01); *A61K 8/8147* (2013.01); *A61Q 5/06* (2013.01); *B65D 83/20* (2013.01); *B65D 83/28* (2013.01); *B65D 83/753* (2013.01); *A61K 2800/31* (2013.01); *A61K 2800/87* (2013.01); *B05B 1/14* (2013.01); *B65D 83/206* (2013.01)

(58) Field of Classification Search
None
See application file for complete search history.

(56) References Cited

U.S. PATENT DOCUMENTS

| | | | |
|---|---|---|---|
| 2,047,398 | A | 7/1936 | Voss et al. |
| 2,102,113 | A | 12/1937 | Djordjevitch |
| 2,723,248 | A | 11/1955 | Wright |
| 3,161,460 | A | 12/1964 | Huber |
| 3,504,862 | A | 4/1970 | Lowry |
| 3,579,629 | A | 5/1971 | Pasero et al. |
| 3,589,978 | A | 6/1971 | Kamal et al. |
| 3,628,733 | A | 12/1971 | Kahn |
| 3,716,633 | A | 2/1973 | Viout et al. |
| 3,767,125 | A | 10/1973 | Gehres et al. |
| 3,792,068 | A | 2/1974 | Luedders et al. |
| 3,810,977 | A | 5/1974 | Levine et al. |
| 3,836,537 | A | 9/1974 | Boerwinkle et al. |
| 3,910,862 | A | 10/1975 | Barabas et al. |
| 3,925,542 | A | 12/1975 | Viout et al. |
| 3,946,749 | A | 3/1976 | Papantoniou |

(Continued)

FOREIGN PATENT DOCUMENTS

| | | | |
|---|---|---|---|
| DE | 2330956 A1 | 1/1974 | |
| DE | 102005025016 | * 12/2005 | ................ B01F 7/04 |

(Continued)

OTHER PUBLICATIONS

Oscar Blandi. http://www.skinstore.com/p-6885-oscar-blandi-pronto-dry-shampoo-spray.aspx. Published Jun. 13, 2011.*
DE102005025016 Eng Tran.*
WO2004043608 Eng Tran.*
International Search Report for PCT/EP2014/058896, dated Sep. 23, 2014.
International Search Report and Written Opinion for PCT/EP2014/058892, dated Oct. 29, 2014.
International Search Report for PCT/EP2014/058894, dated Sep. 29, 2014.
English language abstract for EP 0080976 A1 (Jun. 8, 1983).
English language abstract for FR 2357241 A2 (Feb. 3, 1978).

(Continued)

*Primary Examiner* — Nicole P Babson
*Assistant Examiner* — Lori K Mattison
(74) *Attorney, Agent, or Firm* — The Marbury Law Group, PLLC (57) ABSTRACT

The present invention relates to an aerosol device including: —a container containing: —one or more propellants, and —a composition including one or more fixing polymers and/or one or more styling powders including one or more water-insoluble inorganic compounds, the propellant or propellants possibly being present in the composition or in the container, separate from the composition, —an aerosol device for distributing the aerosol composition, including a diffuser having at least three spraying apertures for spraying the composition in a main spraying direction. The invention further provides a method for shaping the hair and/or maintaining the style, including a step of applying to the wet or dry hair a cosmetic composition sprayed from a specific aerosol device.

19 Claims, 1 Drawing Sheet

(56) References Cited

U.S. PATENT DOCUMENTS

| | | | |
|---|---|---|---|
| 3,966,403 A | 6/1976 | Papantoniou et al. |
| 3,966,404 A | 6/1976 | Papantoniou et al. |
| 3,990,459 A | 11/1976 | Papantoniou |
| 4,031,307 A | 6/1977 | DeMartino et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,165,367 A | 8/1979 | Chakrabarti |
| 4,223,009 A | 9/1980 | Chakrabarti |
| 4,282,203 A | 8/1981 | Jacquet et al. |
| 4,389,752 A | 6/1983 | Briner et al. |
| 4,401,271 A | 8/1983 | Hansen |
| 4,450,151 A | 5/1984 | Shinozawa |
| 4,557,916 A | 12/1985 | Withiam |
| 4,605,553 A | 8/1986 | Passalacqua |
| 4,693,925 A | 9/1987 | Cheung et al. |
| 4,728,571 A | 3/1988 | Clemens et al. |
| 4,822,596 A | 4/1989 | Callingham et al. |
| 4,871,529 A | 10/1989 | Sramek |
| 4,874,554 A | 10/1989 | Lange et al. |
| 4,957,732 A | 9/1990 | Grollier et al. |
| 4,972,037 A | 11/1990 | Garbe et al. |
| 4,983,377 A | 1/1991 | Murphy et al. |
| 5,297,739 A | 3/1994 | Allen |
| 5,300,282 A | 4/1994 | King |
| 5,508,259 A | 4/1996 | Holzner et al. |
| 5,538,717 A | 7/1996 | La Poterie |
| 5,614,173 A | 3/1997 | Ulmer et al. |
| 5,643,557 A | 7/1997 | Eteve et al. |
| 5,690,924 A | 11/1997 | Keil et al. |
| 5,879,669 A | 3/1999 | Clausen et al. |
| 6,106,813 A | 8/2000 | Mondet et al. |
| 6,166,093 A | 12/2000 | Mougin et al. |
| 6,210,689 B1 | 4/2001 | Martino et al. |
| 6,245,324 B1 | 6/2001 | Hough et al. |
| 6,319,959 B1 | 11/2001 | Mougin et al. |
| 6,350,434 B1 | 2/2002 | Bhatt et al. |
| 6,372,876 B1 | 4/2002 | Kim et al. |
| 6,395,265 B1 | 5/2002 | Mougin et al. |
| 6,415,992 B1 * | 7/2002 | Blondeel ............... A61H 9/00 |
| | | 222/394 |
| 6,589,509 B2 | 7/2003 | Keller et al. |
| 6,751,886 B2 | 6/2004 | Chang et al. |
| 7,063,834 B2 | 6/2006 | Mougin et al. |
| 7,585,824 B2 | 9/2009 | Popplewell et al. |
| 10,440,140 B2 | 10/2019 | Barraclough et al. |
| 10,532,880 B2 | 1/2020 | Smail et al. |
| 2002/0017575 A1 | 2/2002 | Andrews et al. |
| 2002/0031478 A1 | 3/2002 | Keller et al. |
| 2002/0150546 A1 | 10/2002 | Mougin et al. |
| 2003/0150624 A1 * | 8/2003 | Rummel ............... B01F 5/0413 |
| | | 169/43 |
| 2003/0150937 A1 | 8/2003 | Laidler et al. |
| 2003/0163878 A1 | 9/2003 | Pruche |
| 2003/0185777 A1 | 10/2003 | Banowski et al. |
| 2003/0191271 A1 | 10/2003 | Mondet et al. |
| 2004/0047812 A1 | 3/2004 | Pataut et al. |
| 2004/0170575 A1 | 9/2004 | Belli et al. |
| 2004/0175404 A1 | 9/2004 | Shefer et al. |
| 2005/0163737 A1 | 7/2005 | Lemoine et al. |
| 2005/0220723 A1 | 10/2005 | Benabdillah et al. |
| 2005/0224524 A1 | 10/2005 | Khan et al. |
| 2008/0019928 A1 | 1/2008 | Franzke et al. |
| 2008/0274071 A1 | 11/2008 | Kaplan et al. |
| 2009/0061004 A1 | 3/2009 | Birkel et al. |
| 2009/0218418 A1 | 9/2009 | Sharief |
| 2010/0040572 A1 | 2/2010 | Mougin |
| 2012/0097180 A1 * | 4/2012 | Harris ............... B65D 83/206 |
| | | 132/200 |
| 2012/0171264 A1 | 7/2012 | Bernet et al. |
| 2012/0258052 A1 | 10/2012 | Mueller et al. |
| 2012/0282190 A1 | 11/2012 | Hammer |
| 2013/0340786 A1 | 12/2013 | Rodrigues et al. |
| 2014/0030196 A1 | 1/2014 | Russell et al. |
| 2014/0079747 A1 | 3/2014 | Dihora et al. |
| 2015/0014443 A1 | 1/2015 | Albisetti |
| 2015/0041559 A1 | 2/2015 | Albisetti |
| 2015/0104397 A1 | 4/2015 | Smail et al. |
| 2015/0122833 A1 | 5/2015 | Baudin |
| 2015/0139917 A1 | 5/2015 | Gawtrey et al. |
| 2016/0075501 A1 | 3/2016 | Aubert et al. |
| 2016/0100667 A1 | 4/2016 | Aubert et al. |
| 2016/0106634 A1 | 4/2016 | Gawtrey et al. |
| 2018/0000700 A1 | 1/2018 | Smail et al. |
| 2018/0243763 A1 | 8/2018 | Eurippini |

FOREIGN PATENT DOCUMENTS

| | | |
|---|---|---|
| DE | 102008035013 A1 | 1/2010 |
| EP | 0080976 A1 | 6/1983 |
| EP | 0095238 A2 | 11/1983 |
| EP | 0186507 A2 | 7/1986 |
| EP | 0342834 A2 | 11/1989 |
| EP | 0412704 A2 | 2/1991 |
| EP | 0412707 A1 | 2/1991 |
| EP | 0452208 A1 | 10/1991 |
| EP | 0530974 A1 | 3/1993 |
| EP | 0582152 A2 | 2/1994 |
| EP | 0619111 A1 | 10/1994 |
| EP | 0637600 A1 | 2/1995 |
| EP | 0648485 A1 | 4/1995 |
| EP | 0751162 A1 | 1/1997 |
| EP | 0 974 332 A1 | 1/2000 |
| EP | 1026220 A1 | 8/2000 |
| EP | 1407754 A1 | 4/2004 |
| EP | 2444160 A1 | 4/2012 |
| EP | 2777770 A1 | 9/2014 |
| FR | 1222944 A | 6/1960 |
| FR | 1400366 A | 5/1965 |
| FR | 1564110 A | 3/1968 |
| FR | 1578989 A | 8/1969 |
| FR | 1580545 A | 9/1969 |
| FR | 1600138 A | 7/1970 |
| FR | 2077143 A | 10/1971 |
| FR | 2198719 A1 | 4/1974 |
| FR | 2265781 A1 | 10/1975 |
| FR | 2265782 A1 | 10/1975 |
| FR | 2350384 A1 | 12/1977 |
| FR | 2357241 A2 | 2/1978 |
| FR | 2393573 A1 | 1/1979 |
| FR | 2434194 A1 | 3/1980 |
| FR | 2439798 A1 | 5/1980 |
| FR | 2589476 A1 | 5/1987 |
| FR | 2715841 A1 | 8/1995 |
| FR | 2743297 A1 | 7/1997 |
| FR | 2814943 A1 | 4/2002 |
| FR | 2924341 A1 | 6/2009 |
| FR | 2980125 A1 | 3/2013 |
| FR | 2985201 A1 | 7/2013 |
| FR | 2985202 A1 | 7/2013 |
| FR | 2990131 A1 | 11/2013 |
| FR | 2990133 A1 | 11/2013 |
| FR | 3004901 A1 | 10/2014 |
| FR | 3004902 A1 | 10/2014 |
| FR | 3004929 A1 | 10/2014 |
| FR | 3031437 A1 | 7/2016 |
| GB | 839805 A | 6/1960 |
| GB | 922457 A | 4/1963 |
| GB | 1021400 A | 3/1966 |
| GB | 1218222 A | 1/1971 |
| GB | 1235908 A | 6/1971 |
| GB | 1331819 A | 9/1973 |
| GB | 1408388 A | 10/1975 |
| GB | 1572626 A | 7/1980 |
| GB | 2340891 A | 3/2000 |
| JP | 2003-326197 A | 11/2003 |
| JP | 2004-161339 A | 6/2004 |
| LU | 75370 A1 | 2/1978 |
| LU | 75371 A1 | 2/1978 |
| WO | 93/23009 A1 | 11/1993 |
| WO | 94/03510 A1 | 2/1994 |
| WO | 95/00578 A1 | 1/1995 |
| WO | 98/43599 A1 | 10/1998 |

(56) References Cited

FOREIGN PATENT DOCUMENTS

| WO | 02/078653 | A1 | 10/2002 |
|---|---|---|---|
| WO | 02/096379 | A1 | 12/2002 |
| WO | 03/045573 | A1 | 6/2003 |
| WO | 03/049711 | A2 | 6/2003 |
| WO | 2004/043608 | A1 | 5/2004 |
| WO | 2011/019539 | A2 | 2/2011 |
| WO | 2011/056625 | A1 | 5/2011 |
| WO | 2012/080255 | A1 | 6/2012 |
| WO | 2013/064918 | A1 | 5/2013 |
| WO | 2013/167530 | A2 | 11/2013 |
| WO | 2013/167536 | A2 | 11/2013 |
| WO | 2014/177647 | A2 | 11/2014 |
| WO | 2014/177649 | A1 | 11/2014 |
| WO | 2016/001190 | A1 | 1/2016 |
| WO | 2016/005703 | A1 | 1/2016 |
| WO | 2016/066729 | A1 | 5/2016 |
| WO | 2016/066730 | A1 | 5/2016 |
| WO | 2016/092109 | A1 | 6/2016 |
| WO | 2016/110575 | A1 | 7/2016 |
| WO | 2016/110578 | A1 | 7/2016 |
| WO | 2016/110579 | A1 | 7/2016 |
| WO | 2018/162701 | A1 | 9/2018 |
| WO | 2018/162707 | A1 | 9/2018 |
| WO | 2018/162711 | A1 | 9/2018 |

OTHER PUBLICATIONS

English language abstract for FR 2980125 A1 (Mar. 22, 2013).
English language abstract for JP 2004-161339 A (Jun. 10, 2004).
English language abstract for WO 02/078653 A1 (Oct. 10, 2002).
Brunauer, Stephen et al., "Adsorption of Gases in Multimolecular Layers," Journal of the American Chemical Society, vol. 60, Feb. 1938, p. 309-319.
International Search Report for counterpart Application No. PCT/EP2013/0509382, dated Jun. 20, 2014.
International Search Report for counterpart Application No. PCT/EP2013/059393, dated Jun. 20, 2014.
Database WPI Week 201172, Thomas Scientific, London, GB, AN 2011-N36295, XP002690571 (Jan. 25, 2013).
Mintel: Apr. 2010, "Refresh Dry Shampoo".
Mintel: Jun. 2011, "Brown Hair Powder Shampoo".
Non-Final Office Action for co-pending U.S. Appl. No. 14/399,753, dated Sep. 8, 2015.
Final Office Action for co-pending U.S. Appl. No. 14/399,753, dated Mar. 30, 2016.
Non-Final Office Action for co-pending U.S. Appl. No. 14/399,764, dated Dec. 17, 2015.
Final Office Action for co-pending U.S. Appl. No. 14/399,764, dated Aug. 5, 2016.
Non-Final Office Action for copending U.S. Appl. No. 14/399,764, dated Mar. 8, 2017.
Non-Final Office Action for copending U.S. Appl. No. 14/888,013, dated Apr. 13, 2017.
Non-Final Office Action for copending U.S. Appl. No. 14/787,983, dated Sep. 15, 2016.
Final Office Action for co-pending U.S. Appl. No. 14/399,753, dated Sep. 30, 2016.
Notice of Allowance for co-pending U.S. Appl. No. 15/541,738, dated Sep. 4, 2019.
Supplemental Notice of Allowance for co-pending U.S. Appl. No. 15/523,242, dated Sep. 5, 2019.
Non-Final Office Action for co-pending U.S. Appl. No. 15/322,771, dated Sep. 6, 2019.
Mintel: "Clean Freak Refreshing Dry Shampoo," XP007923188, Demert Brands, Mar. 2014.
Final Office Action for co-pending U.S. Appl. No. 14/399,764, dated Jun. 7, 2019.
Notice of Allowance for co-pending U.S. Appl. No. 15/523,242, dated Jun. 12, 2019.
Final Office Action for copending U.S. Appl. No. 14/787,983, dated May 30, 2017.
International Search Report for counterpart Application PCT/FR2015/051896, dated Oct. 19, 2015.
International Search Report for counterpart Application PCT/EP2015/075061, dated Jan. 20, 2016.
Internatioal Search Report for counterpart Application PCT/EP2015/075062, dated Jan. 26, 2016.
MINTEL: "Code 10 Hair Styling Cream," XP007923186, Sep. 2001.
MINTEL: "One More Day Dry Shampoo," XP 007923187, Aug. 2013.
MINTEL: "Foot Deodorant Spray," XP007923193, Oct. 2013.
MINTEL: "72h Anti-Perspirant Deodorant," XP007923192, Jan. 2014.
MINTEL: "Dry Shampoo," XP007923191, Jan. 2014.
Non-Final Office Action for copending U.S. Appl. No. 15/324,804, dated Mar. 5, 2018.
Non-Final Office Action for copending U.S. Appl. No. 15/523,232, dated Feb. 23, 2018.
Bezard et al., "Triglycerides of Coconut Oil," Journal of American Oil Society, 48, 3, Mar. 1971, pp. 134-139.
Non-Final Office Action for copending U.S. Appl. No. 15/523,242, dated Aug. 31, 2017.
Final Office Action for copending U.S. Appl. No. 14/888,013, dated Aug. 15, 2017.
Final Office Action for copending U.S. Appl. No. 14/399,764, dated Aug. 16, 2017.
Non-Final Office Action for copending U.S. Appl. No. 14/399,753, dated Oct. 4, 2017.
Non-Final Office Action for copending U.S. Appl. No. 14/787,983, dated May 11, 2018.
Non-Final Office Action for copending U.S. Appl. No. 15/523,242, dated Mar. 27, 2018.
International Search Report for counterpart Application PCT/EP2011/072617, dated Jul. 5, 2012.
Todd, Charles, et al., "Volatile Silicone Fluids for Cosmetic Formulations," Cosmetics and Toiletries, vol. 91, Jan. 1976, pp. 29-32.
International Search Report for counterpart Application PCT/EP2016/050295, dated Mar. 23, 2016.
International Search Report for counterpart Application PCT/EP2015/050299, dated Mar. 23, 2016.
International Search Report for counterpart Application PCT/EP2016/050300, dated Mar. 16, 2016.
Non-Final Office Action for copending U.S. Appl. No. 15/541,738, dated May 17, 2018.
Non-Final Office Action for copending U.S. Appl. No. 13/993,413, dated May 19, 2015.
Final Office Action for copending U.S. Appl. No. 13/993,413, dated Dec. 30, 2015.
Non-Final Office Action for copending U.S. Appl. No. 13/993,413, dated Nov. 8, 2017.
Final Office Action for copending U.S. Appl. No. 13/993,413, dated Jul. 5, 2018.
Oxford Dictionary, Half-Ester, http://www.oxfordreference.com/view/10.1093/acref/9780198529170.001.0001/acref-9780198529170-e-8589, retrieved online on Oct. 19, 2017 (Year:2017).
Final Office Action for copending U.S. Appl. No. 13/993,413, dated Nov. 14, 2016.
Final Office Action for copending U.S. Appl. No. 14/787,983, dated Dec. 27, 2018.
Final Office Action for copending U.S. Appl. No. 15/523,232, dated Jan. 25, 2019.
Non-Final Office Action for copending U.S. Appl. No. 15/541,738, dated Feb. 5, 2019.
Non-Final Office Action for copending U.S. Appl. No. 15/541,741, dated Feb. 27, 2019.
International Search Report for counterpart Application No. PCT/EP2015/064780, dated Sep. 14, 2015.
Porter, M.R., "Handbook of Surfactants," published by Blackie & Son (Glasgow and London), 1991, pp. 116-178.
MINTEL: "Styling Mousse," XP002736036, Nov. 2008.

(56) References Cited

OTHER PUBLICATIONS

Non-Final Office Action for co-pending U.S. Appl. No. 14/888,013, dated Mar. 14, 2019.
Non-Final Office Action for co-pending U.S. Appl. No. 14/787,983, dated Jun. 26, 2019.
Final Office Action for co-pending U.S. Appl. No. 15/541,741, dated Jul. 11, 2019.
Non-Final Office Action for co-pending U.S. Appl. No. 15/541,741, dated Mar. 3, 2020.
Clearco, "Cyclo-1400-DM D5 Cyclomethicone/dimethicone blend," ([retrieved from on-line website: http://www.clearcoproducts.com/cyclo-1400-d5-blend.html], 2013, pp. 1-2.
Wayback Machine to support publication year of Clearco (Year: 2013).
Non-Final Office Action for co-pending U.S. Appl. No. 15/523,232, datedd Feb. 20, 2020.
Final Office Action for co-pending U.S. Appl. No. 14/787,983, dated Feb. 26, 2020.
Final Office Action for copending U.S. Appl. No. 15/324,804, dated Apr. 20, 2020.
Notice of Allowance for copending U.S. Appl. No. 15/541,743, dated Mar. 18, 2020.
Non-Final Office Action for copending U.S. Appl. No. 15/322,771, dated Mar. 20, 2020.
Non-Final Office Action for co-pending U.S. Appl. No. 15/324,804, dated Oct. 10, 2019.
Final Office Action for co-pending U.S. Appl. No. 14/888,013, dated Oct. 18, 2019.
Non-Final Office Action for co-pending U.S. Appl. No. 15/541,743, dated Nov. 21, 2019.
Final Office Action for copending U.S. Appl. No. 15/322,771, dated Jul. 10, 2020.
Non-Final Office Action for copending U.S. Appl. No. 14/787,983, dated Jul. 15, 2020.
Final Office Action for copending U.S. Appl. No. 14/787,983, dated Feb. 19, 2021.
Non-Final Office Action for copending U.S. Appl. No. 15/322,771, dated Mar. 2, 2021.
Non-Final Office Action for copending U.S. Appl. No. 14/888,013, dated May 11, 2021.
Non-Final Office Action for copending U.S. Appl. No. 15/541,741, dated May 27, 2021.
International Search Report and Written Opinion for counterpart Application No. PCT/EP2018/055882, dated May 4, 2018.
International Search Report and Written Opinion for counterpart Application No. PCT/EP2018/055889, dated May 4, 2018.
International Search Report and Written Opinion for counterpart Application No. PCT/EP2018/055904, dated Apr. 30, 2018.
Final Office Action for copending U.S. Appl. No. 16/491,375, dated May 26, 2020.
Non-Final Office Action for copending U.S. Appl. No. 16/491,375, dated Nov. 25, 2019.
Non-Final Office Action for copending U.S. Appl. No. 16/491,372, dated May 28, 2020.
MPL search string: IQQueryQuickExport 202005221756, downloaded May 22, 2020.
MPL search string IQQueryQuickExport 202005221759, downloaded May 22, 2020.
Final Office Action for copending U.S. Appl. No. 16/491,372, dated Dec. 18, 2020.
Non-Final Office Action for copending U.S. Appl. No. 16/491,374, dated Jan. 14, 2021.
Final Office Action for copending U.S. Appl. No. 15/541,741, dated Sep. 17, 2020.
Final Office Action for copending U.S. Appl. No. 15/523,232, dated Oct. 1, 2020.
Final Office Action for copending U.S. Appl. No. 16/491,374, dated Jun. 28, 2021.
Non-Final Office Action for copending U.S. Appl. No. 16/491,372, dated Jul. 12, 2021.
Final Office Action for copending U.S. Appl. No. 14/888,013, dated Sep. 9, 2021.
Non-Final Office Action for copending U.S. Appl. No. 16/491,374, dated Oct. 20, 2021.
Non-Final Office Action for copending U.S. Appl. No. 14/888,013, dated Jun. 14, 2022.

* cited by examiner

AEROSOL DEVICE WITH MULTI-APERTURE DIFFUSION FOR HAIR SHAPING AND/OR STYLE HOLDING

CROSS REFERENCE TO RELATED APPLICATION

This is a national stage application of PCT/EP2014/058896, filed internationally on Apr. 30, 2014, which claims priority to French Application No. 1354013, filed on Apr. 30, 2013, all of which are incorporated herein by their entireties.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILED VIA THE OFFICE ELECTRONIC FILING SYSTEM

Not Applicable

STATEMENT REGARDING PRIOR DISCLOSURES BY THE INVENTOR OR A JOINT INVENTOR

Not Applicable

BACKGROUND OF THE INVENTION

The present invention relates to an aerosol device comprising a cosmetic composition based on at least one fixing polymer and/or on at least one styling powder, comprising at least one water-insoluble inorganic compound, and to the use thereof in the cosmetic treatment of the hair, particularly for shaping the hair and/or for maintaining the style.

The hair products for shaping and/or holding the hair style that are the most widespread on the cosmetics market are spray compositions, such as lacquers and sprays. They are composed essentially of an alcoholic or aqueous solution and of one or more materials, generally polymeric resins, also referred to as fixing components, whose function is to form joins between the individual hairs, in a blend with various cosmetic adjuvants.

These products provide for fixing and for holding of the hair style over time. In practice, however, these products are not entirely satisfactory, particularly in terms of application. The conventionally employed aerosol sprays produce a conical spray which is not ideal for localized application.

There is therefore a need for development of a new aerosol device comprising a hair shaping composition that facilitates the shaping of the hair style and produces effective fixing of the hair style while limiting the amount of fixing and/or styling agents that are used.

The applicant has found, surprisingly and advantageously, that the use of a means for distributing said aerosol composition that comprises a diffuser having at least two spraying apertures for distributing a composition comprising at least one fixing polymer and/or at least one styling powder comprising at least one water-insoluble inorganic compound allows a hair style to be obtained easily and rapidly with volume and with texturing.

BRIEF SUMMARY OF THE INVENTION

The invention accordingly provides an aerosol device comprising:
a container containing:
one or more propellants, and
a composition comprising one or more fixing polymers and/or one or more styling powders comprising one or more water-insoluble inorganic compounds,
the propellant or propellants possibly being present in the composition or in the container, separate from the composition,
a means for distributing said aerosol composition, comprising a diffuser having at least three spraying apertures for spraying the composition in a main spraying direction.

This particular combination allows the hair style to be shaped easily and rapidly.

It also facilitates the application and the distribution of the hair care composition over the body of hair in a uniform manner, and thus provides high performance in terms of fixing, while limiting the amount of fixing and/or styling agents that are used. The composition according to the invention therefore allows the hair to be fixed appropriately, thus leading to satisfactory shaping and/or satisfactory style holding.

It also allows the maintenance of the hair style over time to be improved.

The present invention also relates to a method for shaping the hair and/or maintaining the style, comprising a step of applying to the wet or dry hair a cosmetic composition sprayed from an aerosol device according to the invention, to be rinsed off or not, after an optional leave-on time or after optional drying.

The invention further provides for the use of the cosmetic composition sprayed from this aerosol device for shaping the hair and/or for maintaining the style.

Further objects, features, aspects and advantages of the invention will become even more clearly apparent from the reading of the description and example which follows.

DETAILED DESCRIPTION OF THE INVENTION

In the text below, unless otherwise indicated, the end points of a range of values are included in that range, particularly in the expressions "of between" and "of from . . . to . . . ".

Moreover, the expression "at least one" as used in the present description is equivalent to the expression "one or more".

According to the invention, the aerosol device comprises a container which contains a cosmetic composition comprising one or more fixing polymers and/or one or more styling powders comprising one or more water-insoluble inorganic compounds.

The cosmetic composition according to the invention may comprise at least one fixing polymer.

For the purposes of the invention, a fixing polymer is any polymer which is able, by application to the hair, to impart a shape to the body of hair or to maintain a shape that has already been acquired.

The fixing polymer or polymers used are selected from ionic, especially anionic, cationic, amphoteric, and nonionic fixing polymers, and mixtures thereof.

Anionic polymers include polymers containing groups derived from carboxylic, sulfonic or phosphoric acids, and having a number-average molecular mass of between 500 and 5 000 000.

The carboxylic groups are provided by unsaturated monocarboxylic or dicarboxylic acid monomers, such as those conforming to the following formula:

(I)

in which n is an integer from 0 to 10, A denotes a methylene group which is optionally connected to the carbon atom of the unsaturated group or to the neighbouring methylene group when n is greater than 1, via a heteroatom such as oxygen or sulfur, $R_1$ denotes a hydrogen atom or a phenyl or benzyl group, $R_2$ denotes a hydrogen atom, an alkyl group containing 1 to 4 carbon atoms, or a carboxyl group, $R_3$ denotes a hydrogen atom, an alkyl group containing 1 to 4 carbon atoms, or a —$CH_2$—COOH, phenyl or benzyl group.

In the formula (I) above, the alkyl group containing 1 to 4 carbon atoms may more particularly denote methyl and ethyl groups.

The anionic fixing polymers containing carboxylic or sulfonic groups that are preferred are:

A) Copolymers of acrylic or methacrylic acid or salts thereof, including copolymers of acrylic acid and acrylamide, and methacrylic acid/acrylic acid/ethyl acrylate/methyl methacrylate copolymers, more particularly Amerhold DR 25 sold by the company Amerchol, and sodium salts of polyhydroxycarboxylic acids. Mention may also be made of methacrylic acid/ethyl acrylate copolymers, in particular in aqueous dispersion, such as Luviflex Soft and Luvimer MAE, which are sold by the company BASF.

B) Copolymers of acrylic or methacrylic acids with a monoethylenic monomer such as ethylene, styrene, vinyl esters, acrylic or methacrylic esters, which are optionally grafted on a polyalkylene glycol such as polyethylene glycol, and are optionally crosslinked. Such polymers are described in particular in French patent 1 222 944 and German patent application 2 330 956, the copolymers of this type comprising an optionally N-alkylated and/or hydroxyalkylated acrylamide unit in their chain as described especially in Luxembourg patent applications 75370 and 75371. Mention may also be made of copolymers of acrylic acid and $C_1$-$C_4$ alkyl methacrylate.

As another anionic fixing polymer from this class, mention may also be made of the branched sequenced anionic butyl acrylate/acrylic acid/methacrylic acid polymer sold under the name Fixate G-100 L of the company Lubrizol (INCI name AMP-ACYLATES/ALLYL METHACRYLATE COPOLYMER).

C) Copolymers derived from crotonic acid, such as those including in their chain vinyl propionate or acetate units, and optionally other monomers such as allyl or methallyl esters, vinyl ethers or vinyl esters of a linear or branched, saturated carboxylic acid with a long hydrocarbon chain, such as those containing at least 5 carbon atoms, it being possible optionally for these polymers to be grafted and crosslinked, or else a vinyl, allyl or methallyl ester of an α- or β-cyclic carboxylic acid. Such polymers are described, inter alia, in French patents 1 222 944, 1 580 545, 2 265 782, 2 265 781, 1 564 110 and 2 439 798. Commercial products that fall within this category are the resins 28-29-30, 26-13-14 and 28-13-10 sold by the company National Starch.

Mention may also be made, as copolymer derived from crotonic acid, of crotonic acid/vinyl acetate/vinyl tert-butylbenzoate terpolymers, and more particularly Mexomere PW supplied by the company Chimex.

D) Copolymers of monounsaturated C4-C8 carboxylic acids or anhydrides, in particular polymers derived from maleic, fumaric and/or itaconic acids or anhydrides with vinyl esters, vinyl ethers, vinyl halides, phenylvinyl derivatives, acrylic acid and its esters; these polymers may be esterified. Polymers of these kinds are described more particularly in U.S. Pat. Nos. 2,047,398, 2,723,248 and 2,102,113, and in patent GB 839 805, and in particular are those sold under the names Gantrez® AN or ES by the company ISP.

Polymers also falling within this category are the copolymers of maleic, citraconic and/or itaconic anhydrides and of an allylic or methallylic ester optionally comprising an acrylamide or methacrylamide group, an α-olefin, acrylic or methacrylic esters, acrylic or methacrylic acids or vinylpyrrolidone in their chain, the anhydride functions being monoesterified or monoamidated. These polymers are described, for example, in French patents 2 350 384 and 2 357 241 by the Applicant.

E) Polyacrylamides containing carboxylate groups.

F) Polymers containing sulfonic groups. These polymers may be polymers comprising vinylsulfonic, styrenesulfonic, naphthalenesulfonic, acrylamidoalkylsulfonic and/or sulfoisophtalate units.

These polymers can in particular be chosen from:
polyvinylsulfonic acid salts with a molecular mass of between about 1000 and 100 000, and also copolymers with an unsaturated comonomer such as acrylic or methacrylic acids and esters thereof, and also acrylamide or derivatives thereof, vinyl ethers and vinylpyrrolidone;
polystyrenesulfonic acid salts, sodium salts, with a molecular mass of about 500 000 and of about 100 000. These compounds are described in patent FR 2198719;
polyacrylamidesulfonic acid salts such as those mentioned in U.S. Pat. No. 4,128,631.

G) Grafted anionic silicone polymers.

The grafted silicone polymers used are preferably chosen from polymers containing a non-silicone organic backbone grafted with monomers containing a polysiloxane, polymers containing a polysiloxane backbone grafted with non-silicone organic monomers, and mixtures thereof.

H) Anionic polyurethanes, possibly comprising silicone grafts and silicones containing hydrocarbon grafts.

Examples of fixing polyurethanes include, in particular, the dimethylolpropionic acid/isophorone diisocyanate/neopentyl glycol/polyesterdiol copolymer (also known under the name polyurethane-1, INCI nomenclature) sold under the brand name Luviset® PUR by the company BASF, and the dimethylolpropionic acid/isophorone diisocyanate/neopentyl glycol/polyesterdiol/silicone diamine copolymer (also known under the name polyurethane-6, INCI nomenclature) sold under the brand name Luviset® Si PUR A by the company BASF.

Another anionic polyurethane that can also be used is Avalure UR 450.

It is also possible to use polymers containing sulfoisophthalate groups, such as the polymers AQ55 and AQ48 sold by the company Eastman.

According to the invention, the anionic polymers are preferably selected from copolymers of acrylic acid such as the acrylic acid/ethyl acrylate/N-tert-butylacrylamide terpolymers sold under the name Ultrahold Strong® by the company BASF, and methacrylic acid/ethyl acrylate copolymers, especially in aqueous dispersion, such as Luviflex Soft and Luvimer MAE, which are sold by the company BASF. Copolymers derived from crotonic acid such as vinyl acetate/vinyl tert-butylbenzoate/crotonic acid terpolymers and crotonic acid/vinyl acetate/vinyl neododecanoate terpolymers, which are sold under the name Resin 28-29-30 by the company National Starch; polymers derived from maleic, fumaric and/or itaconic acids or anhydrides with vinyl esters, vinyl ethers, vinyl halides, phenylvinyl derivatives, acrylic acid and its esters, such as the monoesterified maleic anhydride/methyl vinyl ether copolymer sold under the name Gantrez® ES 425 by the company ISP, Luviset SI PUR, Mexomere PW, elastomeric or non-elastomeric anionic polyurethanes, and polymers containing sulfoisophthalate groups.

The cationic fixing polymers that can be used according to the present invention are preferably chosen from polymers comprising primary, secondary, tertiary and/or quaternary amine groups forming part of the polymer chain or directly attached thereto, and having a molecular weight of between 500 and approximately 5 000 000 and preferably between 1000 and 3 000 000.

Among these polymers, mention may be made more particularly of the following cationic polymers:

(1) homopolymers or copolymers derived from acrylic or methacrylic esters or amides and containing at least one of the units of formulae below:

(A)

(B)

(C)

in which:

$R_3$ denotes a hydrogen atom or a $CH_3$ group;

A is a linear or branched alkyl group containing from 1 to 6 carbon atoms, or a hydroxyalkyl group containing from 1 to 4 carbon atoms;

$R_4$, $R_5$ and $R_6$, which are identical or different, represent an alkyl group having from 1 to 18 carbon atoms, or a benzyl group;

$R_1$ and $R_2$, which are identical or different, each represent a hydrogen atom or an alkyl group having from 1 to 6 carbon atoms;

X denotes a methosulfate anion or a halide such as chloride or bromide.

The copolymers of class (1) further contain one or more units deriving from comonomers which may be selected from the class of acrylamides, methacrylamides, diacetonesacrylamides, acrylamides and methacrylamides substituted on the nitrogen by $C_1$-$C_4$ alkyl groups, groups derived from acrylic or methacrylic acids or their esters, vinyl lactams such as vinylpyrrolidone or vinylcaprolactam, and vinyl esters.

Accordingly, these copolymers of class (1) may include the following:

copolymers of acrylamide and dimethylaminoethyl methacrylate quaternized with dimethyl sulfate or with a dimethyl halide, such as that sold under the name Hercofloc® by the company Hercules, copolymers of acrylamide and methacryloyloxyethyltrimethylammonium chloride, described for example in patent application EP-A-080976 and sold under the name Bina Quat P 100 by the company Ciba Geigy, the copolymer of acrylamide and methacryloyloxyethyltrimethylammonium methosulfate, such as that sold under the name Reten by the company Hercules, quaternized or non-quaternized vinylpyrrolidone/dialkylaminoalkyl acrylate or methacrylate copolymers, such as the products sold under the name Gafquat® by the company ISP, such as, for example, Gafquat® 734 or Gafquat® 755, or alternatively the products known as Copolymer® 845, 958 and 937. These polymers are described in detail in French patents 2,077,143 and 2,393,573, polymers containing a fatty chain and a vinylpyrrolidone unit, such as the product sold under the name Styleze W20 and Styleze W10 by the company ISP, dimethylaminoethyl methacrylate/vinylcaprolactam/vinylpyrrolidone terpolymers, such as the product sold under the name Gaffix VC 713 by the company ISP, and quaternized vinylpyrrolidone/dimethylaminopropylmethacrylamide copolymers, such as the products sold under the name Gafquat® HS 100 by the company ISP;

(2) cationic guar gums, preferably containing quaternary ammonium, such as those described in U.S. Pat. Nos.

3,589,578 and 4,031,307, such as guar gums containing trialkylammonium cationic groups. Such products are sold in particular under the trade names Jaguar C13 S, Jaguar C 15 and Jaguar C 17 by the company Meyhall;

(3) quaternary copolymers of vinylpyrrolidone and vinylimidazole;

(4) chitosans or salts thereof; the salts which can be used are more particularly the acetate, lactate, glutamate, gluconate or pyrrolidone carboxylate of chitosan.

These compounds include chitosan having a degree of desacetylation of 90.5% by weight, sold under the name Kytan Brut Standard by the company Aber Technologies, and the chitosan pyrrolidonecarboxylate sold under the name Kytamer® PC by the company Amerchol.

(5) cationic cellulose derivatives such as copolymers of cellulose or of cellulose derivatives that are grafted with a water-soluble monomer containing a quaternary ammonium, and are described in particular in U.S. Pat. No. 4,131,576, such as hydroxyalkylcelluloses, such as hydroxymethyl-, hydroxyethyl- or hydroxy-propylcelluloses grafted in particular with a methacryloyloxyethyltrimethylammonium, methacrylamidopropyl trimethylammonium or dimethyldiallylammonium salt.

The commercialized products which meet this definition are more particularly the products sold under the name "Celquat L 200" and "Celquat H 100" by the National Starch company.

The amphoteric fixing polymers that can be used in accordance with the invention can be chosen from polymers comprising units B and C distributed randomly in the polymer chain, in which B denotes a unit deriving from a monomer comprising at least one basic nitrogen atom and C denotes a unit deriving from an acid monomer comprising one or more carboxylic or sulfonic groups, or alternatively B and C can denote groups deriving from carboxybetaine or sulfobetaine zwitterionic monomers; B and C can also denote a cationic polymer chain comprising primary, secondary, tertiary or quaternary amine groups, in which at least one of the amine groups bears a carboxylic or sulfonic group connected via a hydrocarbon group, or alternatively B and C form part of a chain of a polymer containing an ethylenedicarboxylic unit in which one of the carboxylic groups has been made to react with a polyamine comprising one or more primary or secondary amine groups.

The amphoteric polymers which meet the definition given above and that are more particularly preferred are selected from the following polymers:

(1) Polymers resulting from the copolymerization of a monomer derived from a vinyl compound bearing a carboxylic group, such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkyl methacrylamide and acrylamide. Such compounds are described in U.S. Pat. No. 3,836,537.

The vinyl compound may also be a dialkyldiallylammonium salt such as diethyldiallylammonium chloride.

2) Polymers containing units which derive:

a) from at least one monomer selected from acrylamides or methacrylamides which are substituted on the nitrogen by an alkyl group, b) from at least one acidic comonomer containing one or more reactive carboxylic groups, and c) from at least one basic comonomer, such as esters with primary, secondary, tertiary and quaternary amine substituents of acrylic and methacrylic acids, and the product of quaternization of dimethylaminoethyl methacrylate with dimethyl or diethyl sulfate.

The N-substituted acrylamides or methacrylamides which are more particularly preferred according to the invention are groups in which the alkyl groups contain from 2 to 12 carbon atoms, and more particularly N-ethylacrylamide, N-tert-butylacrylamide, N-tert-octylacrylamide, N-octylacrylamide, N-decylacrylamide, N-dodecylacrylamide, and also the corresponding methacrylamides.

The acidic comonomers are selected more particularly from acrylic, methacrylic, crotonic, itaconic, maleic and fumaric acids and also the alkyl monoesters having 1 to 4 carbon atoms of maleic or fumaric acid or anhydride. The preferred basic comonomers are aminoethyl, butylaminoethyl, N,N'-dimethylaminoethyl and N-tert-butylaminoethyl methacrylates. The copolymers whose CTFA (4th edition, 1991) name is octylacrylamide/acrylates/butylaminoethyl methacrylate copolymer, such as the products sold under the name Amphomer® or Lovocryl® 47 by the company National Starch, are particularly used.

3) Alkylated and crosslinked polyaminoamides deriving wholly or partly from polyaminoamides of general formula:

$$-\!\!\left[\!\text{CO}-\text{R}_4-\text{CO}-z\right]\!\!- \quad \text{(II)}$$

in which $R_4$ represents a divalent group derived from a saturated dicarboxylic acid, from a mono- or dicarboxylic aliphatic acid with an ethylenically double bond, from an ester of an alcohol having 1 to 6 carbon atoms with these acids, or from a group deriving from the addition of any one of the said acids with a bis-primary amine or bis-secondary-derived amine, and Z denotes a group of a bis-primary or mono- or bis-secondary polyalkylene-polyamine, and preferably represents:

a) in proportions of 60 to 100 mol %, the group $$-\text{NH}-\!\!\left[\!(\text{CH}_2)_x-\text{NH}\right]_p\!- \quad \text{(III)}$$

where x=2 and p=2 or 3, or else x=3 and p=2, this group deriving from diethylenetriamine, triethylenetetramine or dipropylenetriamine;

b) in proportions of 0 to 40 mol %, the group (III) above, in which x=2 and p=1, which derives from ethylenediamine, or the group deriving from piperazine;

c) in proportions of 0 to 20 mol %, the group —NH—(CH2)6-NH— deriving from hexamethylenediamine, these polyaminoamines being crosslinked by addition of a difunctional crosslinking agent selected from epihalohydrins, diepoxides, dianhydrides, bis-unsaturated derivatives, by means of 0.025 to 0.35 mol of crosslinking agent per amine group of the polyaminoamide, and being alkylated by reaction of acrylic acid, chloroacetic acid or an alkane sultone or salts thereof.

The saturated carboxylic acids are preferably selected from acids having 6 to 10 carbon atoms, such as adipic acid, 2,2,4-trimethyladipic acid and 2,4,4-trimethyladipic acid, terephthalic acid, and acids having an ethylenic double bond, such as, for example, acrylic, methacrylic and itaconic acids. The alkane sultones used in the alkylation are preferably propane sultone or butane sultone; the salts of the alkylating agents are preferably the sodium or potassium salts.

4) Polymers containing zwitterionic units of formula:

(IV)

in which $R_5$ denotes a polymerizable unsaturated group, such as an acrylate, methacrylate, acrylamide or methacrylamide group, y and z each represent an integer from 1 to 3, $R_6$ et $R_7$ represent a hydrogen atom or a methyl, ethyl or propyl group, $R_8$ and $R_9$ represent a hydrogen atom or an alkyl group such that the sum of the carbon atoms in $R_{10}$ and $R_{11}$ does not exceed 10.

The polymers comprising such units can also comprise units derived from non-zwitterionic monomers such as dimethyl- or diethylaminoethyl acrylate or methacrylate or alkyl acrylates or methacrylates, acrylamides or methacrylamides or vinyl acetate.

5) Polymers derived from chitosan, containing monomeric units conforming to the following formulae:

(V)

(VI)

(VII)

the unit (V) being present in proportions of between 0% and 30%, the unit (VI) in proportions of between 5% and 50% and the unit (VII) in proportions of between 30% and 90%, subject to the proviso that in this unit F, $R_{10}$ represents a group of formula:

(VIII)

in which, if q=0, $R_{11}$, $R_{12}$ and $R_{13}$, which are identical or different, each represent a hydrogen atom, a methyl, hydroxyl, acetoxy or amino radical, a monoalkylamine radical or a dialkylamine radical which are optionally interrupted by one or more nitrogen atoms and/or optionally substituted by one or more amine, hydroxyl, carboxyl, alkylthio and/or sulfonic groups, an alkylthio radical in which the alkyl group carries an amino radical, with at least one of the groups $R_{17}$, $R_{18}$ and $R_{19}$ in this case being a hydrogen atom;

or, if q=1, $R_{11}$, $R_{12}$ and $R_{13}$ each represent a hydrogen atom, and also the salts formed by these compounds with bases or with acids.

6) Polymers derived from the N-carboxyalkylation of chitosan.

7) Polymers of units conforming to the general formula (IX), which are described, for example, in French patent 1 400 366:

(IX)

in which $R_{14}$ represents a hydrogen atom or a $CH_3O$, $CH_3CH_2O$, or phenyl group, $R_{15}$ denotes hydrogen or a $C_{1-4}$ alkyl group such as methyl and ethyl, $R_{16}$ denotes hydrogen or a $C_{1-4}$ alkyl group such as methyl and ethyl, $R_{17}$ denotes a $C_{1-4}$ alkyl group such as methyl and ethyl or a group conforming to the formula: $-R_{18}-N(R_{16})_2$, with $R_{18}$ representing a $-CH_2-CH_2-$, $-CH_2-CH_2-CH_2-$, or $-CH_2-CH(CH_3)$-group and $R_{16}$ having the meanings given above, and also the higher homologues of these groups, containing up to 6 carbon atoms.

8) Amphoteric polymers of type -D-X-D-X-, selected from:

a) polymers obtained by reaction of chloroacetate acid or sodium choloroacetate with the compounds containing at least one unit of formula:

-D-X-D-X-D- (X)

where D denotes a group and X denotes the symbol E or E', where E or E', which are identical or different, denote a divalent group which is an alkylene group having a straight or branched chain that contains up to 7 carbon atoms in the main chain and is unsubstituted or substituted by hydroxyl groups, and may further comprise oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine and/or alkenylamine groups, hydroxyl, benzylamine, amine oxide, quaternary ammonium, amide, imide, alcohol, ester and/or urethane groups.

b) The polymers of formula:

-D-X-D-X- (XI)

where D denotes a group and X denotes the symbol E or E' and at least once E'; E has the meaning given above, and E' is a divalent group which is an alkylene group having a straight or branched chain having up to 7 carbon atoms in the main chain, and is unsubstituted or substituted by one or more hydroxyl groups and contains one or more nitrogen atoms, the nitrogen atom being substituted by an alkyl chain which is optionally interrupted by an oxygen atom and necessarily contains one or more carboxyl functions or one or more hydroxyl functions, and are betainized by reaction with chloroacetate acid or sodium chloroacetate.

9) ($C_1$-$C_5$)alkyl vinyl ether/maleic anhydride copolymers partly modified by semi-amidification with a N,N-dialkylaminoalkylamine, such as N,N-dimethylaminopropylamine, or by semi-esterification with an N,N-dialkanolamine. These copolymers may also include other vinyl comonomers such as vinylcaprolactam.

According to one preferred embodiment of the invention, the amphoteric fixing polymers that can be used in the aerosol device according to the invention may be selected from branched block copolymers comprising:

(a) nonionic units derived from at least one monomer selected from $C_1$-$C_{20}$, alkyl (meth)acrylates, N-mono-($C_2$-$C_{12}$ alkyl)-(meth)acrylamides and N,N-di-($C_2$-$C_{12}$ alkyl)-(meth)acrylamides, (b) anionic units derived from at least one monomer selected from acrylic acid or methacrylic acid, and (c) polyfunctional units derived from at least one monomer containing at least two polymerizable unsaturated functional groups, and preferably having a structure composed of hydrophobic blocks on which a plurality of more hydrophilic blocks are fixed via polyfunctional units (c).

The amphoteric polymers preferably have at least two glass transition temperatures (Tg), of which at least one is greater than 20° C. and the other is less than 20° C.

The preferred amphoteric polymers are the polymers comprising units deriving:

a) from at least one monomer selected from acrylamides or methacrylamides which are substituted on the nitrogen by an alkyl group, b) from at least one acidic comonomer containing one or more reactive carboxylic groups, and c) from at least one basic comonomer, such as esters with primary, secondary, tertiary and quaternary amine substituents of acrylic and methacrylic acids, and the product of quaternization of dimethylaminoethyl methacrylate with dimethyl or diethyl sulfate.

Mention may be made more particularly of the polymers sold under the name Amphomer by the company National Starch.

The nonionic fixing polymers which can be used according to the present invention are selected, for example, from:
  polyalkyloxazolines;
  vinyl acetate homopolymers;
  vinyl acetate copolymers, such as, for example, copolymers of vinyl acetate and acrylic ester, copolymers of vinyl acetate and ethylene, or copolymers of vinyl acetate and maleic ester, for example dibutyl maleate,
  homopolymers and copolymers of acrylic esters, such as, for example, copolymers of alkyl acrylates and alkyl methacrylates, such as the products provided by the company Rohm & Haas under the names Primal® AC-261 K and Eudragit® NE 30 D, by the company BASF under the name 8845, and by the company Hoechst under the name Appretan® N9212,
  copolymers of acrylonitrile and a nonionic monomer chosen, for example, from butadiene and alkyl (meth)acrylates, such as the products provided under the name CJ 0601 B by the company Rohm & Haas,
  styrene homopolymers,
  styrene copolymers such as, for example, copolymers of styrene and an alkyl (meth)acrylate, such as the products Mowilith® LDM 6911, Mowilith® DM 611 and Mowilith® LDM 6070, which are provided by the company Hoechst, the products Rhodopas® SD 215 and Rhodopas® DS 910, which are provided by the company Rhone Poulenc, copolymers of styrene, alkyl methacrylate and alkyl acrylate, copolymers of styrene and butadiene, or copolymers of styrene, butadiene and vinylpyridine,
  polyamides,
  vinyl lactam homopolymers, such as vinylpyrrolidone homopolymers, and the polyvinylcaprolactam sold under the name Luviskol® Plus by the company BASF,
  vinyl lactam copolymers, such as a poly(vinylpyrrolidone/vinyllactam) copolymer sold under the trade name Luvitec® VPC 55K65W by the company BASF, poly(vinylpyrrolidone/vinyl acetate) copolymers such as those sold under the name PVPVA® S630L by the company ISP, Luviskol® VA 73, VA 64, VA 55, VA 37 and VA 28 by the company BASF, and poly(vinylpyrrolidone/vinyl acetate/vinyl propionate) terpolymers such as, for example, that sold under the name Luviskol® VAP 343 by the company BASF,
  non hydrolysed polyvinylformamide polymers and
  poly(vinyl alcohol)s.

The alkyl groups in the abovementioned nonionic polymers have preferably from 1 to 6 carbon atoms.

The fixing polymer is preferably an anionic, amphoteric or nonionic fixing polymer.

When they are present, the fixing polymer or polymers is or are preferably present in an amount of from 0.1% to 20% by weight, preferably from 0.5% to 8% by weight, more preferably from 1% to 5% by weight, relative to the total weight of the composition, when the propellant or propellants are present in the composition.

The composition may further comprise one or more styling powders comprising one or more water-insoluble inorganic compounds different from sebum-absorbing powders.

A "styling powder" is a powder composed of one or more water-insoluble inorganic compounds exhibiting suitability for the shaping of the body of hair or for the durability of this shaping.

The water-insoluble inorganic compound or compounds is or are selected from metal carbonates, oxides and sulfates and from silicates containing magnesium.

Water-insoluble in the sense of the present invention refers to a compound whose solubility at spontaneous pH in water at 25° C. under atmospheric pressure is less than 0.1%.

Examples include more particularly the carbonates, oxides and sulfates of alkaline earth metals such as beryllium, magnesium, calcium, strontium, barium and radium, more preferably magnesium and calcium; the oxides, sulfates and carbonates of aluminium, gallium and indium; and silicates containing magnesium, more particularly those containing an amount of magnesium of more than 10% by weight (on a dry basis) as expressed in terms of magnesium oxide, such as Li Mg Na silicates, for instance Laponite XLG, which is provided by the company Rockwood.

More preference will be given to using calcium carbonate, magnesium carbonate, alumina, barium sulfate and/or magnesium oxide, and more preferably calcium carbonate such as the calcium carbonate sold under the trade name AH Mikhart 40 by the company Provencale S.A. These compounds preferably have an average particle size of 20 to 50 µm, as water-insoluble inorganic compound(s).

When they are present, the water-insoluble inorganic compound or compounds is or are present in an amount of from 0.1% to 30% by weight, more preferably from 0.5% to 15% by weight, and more preferably still from 1% to 10% by weight, relative to the total weight of the composition, when the propellant or propellants are present in the composition.

The composition may further comprise one or more $C_{2-4}$ monoalcohols.

$C_{2-4}$ monoalcohols which can be used in the aerosol device of the invention include, in particular, ethanol or isopropanol, or better still ethanol.

When they are present, the $C_{2-4}$ monoalcohol or monoalcohols is or are preferably present in an amount of from 1% to 70% by weight, more preferably from 5% to 60% by weight, and more preferably still from 10% to 50% by weight, relative to the total weight of the composition, when the propellant or propellants are present in the composition.

The composition according to the invention may comprise one or more additional organic solvents such as polyols, for instance glycerol, propylene glycol or polyethylene glycols.

It may also comprise water.

The composition according to the invention preferably contains less than 5% by weight of water, relative to the total weight of the composition, when the propellant or propellants are present in the composition. More preferably still it contains no added water. The composition is then referred to as anhydrous.

The container of the device according to the invention likewise comprises one or more propellants.

Examples of propellant which can be used in the aerosol device of the present invention are liquefied gases such as dimethyl ether, chlorinated and/or fluorinated hydrocarbons such as 1,1-difluoroethane, or volatile hydrocarbons such as, in particular, $C_{3-5}$ alkanes, such as propane, isopropane, n-butane, isobutane or pentane, or compressed gases such as air, nitrogen, carbon dioxide, and mixtures thereof.

Mention may be made preferably of dimethyl ether and $C_{3-5}$ alkanes, and more particularly propane, n-butane, isobutane and mixtures thereof.

The agent or agents may be present in the composition or, as a variant, in the container containing the composition, but is or are separate from the composition.

The agent or agents are preferably present in the composition.

When the propellant or propellants are present in the composition, it is or they are preferably present in an amount of from 10% to 90% by weight, more preferably from 15% to 80% by weight, and more preferably still from 20% to 75% by weight, relative to the total weight of the composition.

The compositions defined in the invention may further comprise one or more additives selected from soluble silicones, fatty esters, fatty alcohols, anionic, cationic, non-ionic, amphoteric or zwitterionic conditioning polymers, fragrances, dyes, UV-protective filters, acids, bases, nacres and flakes.

These additives may be present in the composition according to the invention in an amount of from 0% to 20% by weight, relative to the total weight of the composition, when the propellant or propellants are present in the composition.

A person skilled in the art would ensure that these optional additives and their amounts are selected in such a way as to present no detriment to the properties of the compositions of the present invention.

The compositions in accordance with the invention are packaged in an aerosol device comprising a container, also called a reservoir, and a dispensing means.

The container is pressurized and contains the composition to be dispensed. The container containing the pressurized composition can be opaque or transparent. It can be made of glass, of polymer or of metal, optionally covered with a protective lacquer layer.

As already mentioned above, the container contains both the propellant or propellants and the other ingredients of the composition, in a single compartment or, as a variant, in two compartments. According to this latter variant, the container may be composed of an outer aerosol flask comprising an inner pocket hermetically welded to a valve. The various ingredients of the composition are introduced into the inner pocket, and a propellant is introduced between the pocket and the flask, at a pressure sufficient to discharge the product in the form of a spray.

The propellant may be a compressed gas used preferably at a pressure of between 1 and 12 bar, more preferably between 9 and 11 bar.

The container is equipped at its top end with a valve that seals the system. The valves that are suitable for the devices according to the invention are especially valves with an internal restriction aperture of between 0.3 and 3 mm, preferably between 1 and 2.5 mm and even more preferentially between 1.3 and 2 mm, and with a nozzle whose aperture is between 0.2 and 0.6 mm, preferably between 0.3 and 0.5 mm and even more preferentially between 0.35 and 0.45 mm in size.

They are more particularly valves sold by the companies Precision, Coster, Seaquist and Lindal.

The device, conditioned with such a valve, ensures the sealing of the system, and also the dispensing of the product through the diffuser.

Onto this valve is fitted a dispensing means, on which the user can press to make the product come out.

This dispensing means is also known as a diffuser.

The diffuser according to the invention has at least three spraying apertures.

The diffuser preferably has three spraying apertures.

The three spraying apertures are advantageously arranged at 120° from one another, around the spraying direction Y.

The apertures may be single-exit apertures, also called directional apertures, or swirl-ducted apertures.

The spraying apertures may have axes parallel to one another and parallel to the spraying direction Y.

The spraying apertures may terminate in a narrowing of their cross-section. For example, the spraying apertures each comprise a cylindrical section connecting to a corresponding feed duct, a conical section for reducing the cross-section, and a final, low-diameter cylindrical section, from which the composition is ejected.

These apertures are present on one or more nozzles, and preferably on a single nozzle.

Each aperture is supplied by a feed duct, and these ducts open out into a product delivery duct intended to be in communication with the valve.

The feed ducts are preferably inclined obliquely relative to the spraying direction Y.

The term "oblique" should be understood as meaning neither parallel nor perpendicular.

The feed ducts may extend along respective longitudinal axes which are preferably inclined obliquely relative to the axis Y by an angle of 30° and 60°, more preferably of the order of 45°. Preferably, the angle is the same for all the feed ducts.

BRIEF DESCRIPTION OF THE DRAWINGS

The invention may be better understood on reading the following detailed description of a non-limiting implementational example thereof and on examining the appended drawing, in which.

Figure 1:
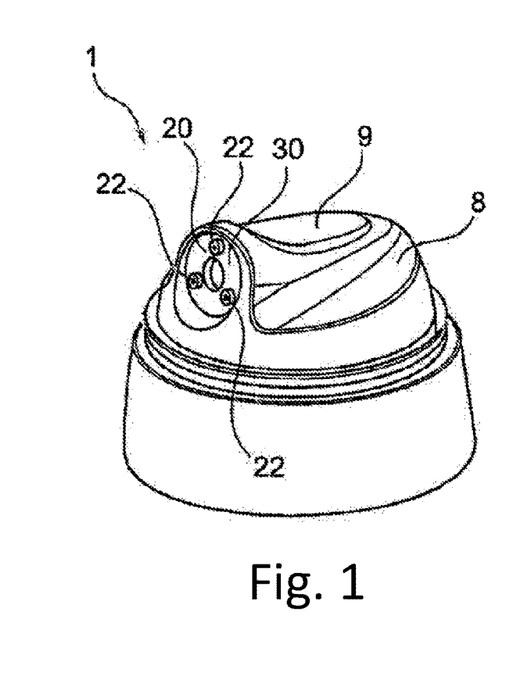
FIG. 1 shows a perspective view in isolation of a diffuser.
Figure 2:
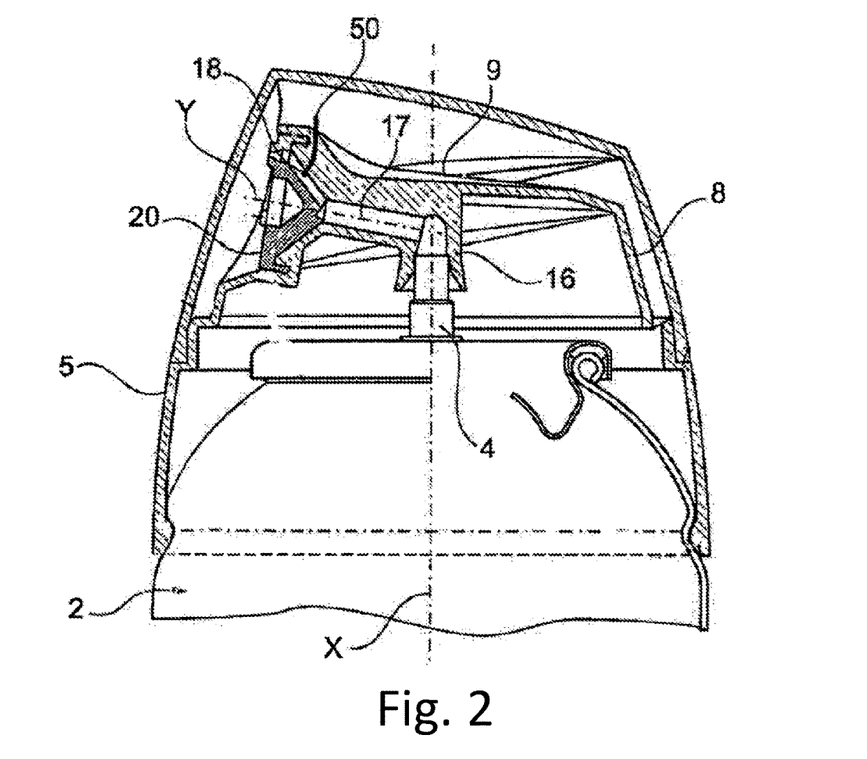
FIG. 2 shows the diffuser mounted on a container with a protective cap in place, in longitudinal, partial and diagrammatic section.
Figure 3:
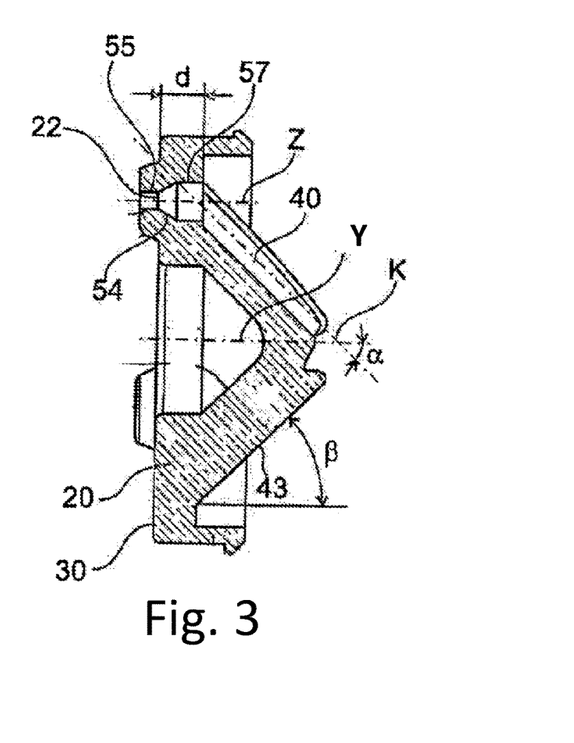
FIG. 3 shows in isolation, in axial section, the spraying nozzle.

The diffuser 1 shown in the figures is intended for attachment to a container 2, for example an aerosol flask containing the composition described above.

The container 2 is equipped with a valve for release by depression of a hollow control rod 4 in the longitudinal axis X of the container. In an alternative form, the valve is for release by tipping.

In the example illustrated, the diffuser 1 comprises a body 5 which includes a push button 8. The push button 8 defines a surface 9 on which the user can press in order to dispense the product.

The push button 8 is produced with a joining piece 16 interlocked over the valve rod 4, this joining piece 16 being in communication with a delivery duct 17, the longitudinal axis Y of which is non-perpendicular to the longitudinal axis X of the container, being inclined upwards, when the container 2 is vertical and the dispensing head 1 is fixed above.

The delivery duct 17 emerges in the bottom of a housing 18, which receives a spraying nozzle 20.

The nozzle 20 has a plurality of spraying apertures 22, in the present case three in number, with axes Z which are parallel to the spraying direction, which is coincident with the longitudinal axis Y of the delivery duct 17 and with the axis of the nozzle.

The apertures 22 emerge on a front face 30 of the nozzle 20, which is visible after the nozzle has been fitted to the push button 8.

In the example illustrated, the nozzle 20 has no swirl ducts; the apertures 22 are directional.

On its back face 43, which has the general form of a dome, the nozzle 20 comprises three grooves 40, each extending longitudinally on an axis K which, with the axis Y of the nozzle 20, forms an angle α of preferably close to 45°.

The grooves 40 define, with the bottom of the housing 18 of the push button 8 which receives them, feed ducts 50 which connect the delivery duct 17 to the spraying apertures 22.

Each feed duct 50 connects to a rotationally generated cylindrical section 57, with an axis Z. A conical section 54 which narrows towards the outlet connects the section 57 to another, rotationally generated cylindrical section 55, with a smaller diameter, which emerges on the front face 30 of the nozzle.

The diameter of the cylindrical section 55 is, for example, 0.25 mm and that of the cylindrical section 57 is 0.6 mm. The axial dimension d of the conical section 54 and of the cylindrical section 57, considered together, is, for example, between 1 and 1.5 mm, for example being 1.3 mm, and the axial dimension of the cylindrical section 55 is, for example, between 0.4 and 0.8 mm, for example being 0.6 mm.

The outer diameter of the nozzle 20 is, for example, less than or equal to 15 mm. The spraying apertures 22 may be relatively close, allowing the formation of a uniform spray at a small distance, for example less than 10 cm from the diffuser 1.

The present invention also relates to a method for shaping the hair and/or maintaining the style, comprising a step of applying to the wet or dry hair a cosmetic composition sprayed from an aerosol device as described above, to be rinsed off or not, after an optional leave-on time or after optional drying.

The present invention also relates to the use of the cosmetic composition defined above and sprayed from the aerosol device according to the invention for shaping the hair and/or maintaining the style.

The example which follows serves to illustrate the invention.

Example

In the example below, all amounts are indicated in weight percentage of product, in terms of active substances, relative to the total weight of the composition.

The compositions below according to the invention were prepared from compounds indicated in the table below.

|  | 1 | 2 |
|---|---|---|
| Calcium carbonate (D50 = 35 μm)[1] | 5% | — |
| Polyvinylcaprolactam[2] | 2% | — |
| Va/crotonates/vinyl neodecanoate copolymer[3] | — | 2.8% |

-continued

|  | 1 | 2 |
|---|---|---|
| Aminomethylpropanol |  | 0.295% |
| Fragrance | 0.1% | 0.3% |
| Isobutane | 60% | — |
| Dimethyl ether | — | 50% |
| Ethanol | qs 100% | qs 100% |

[1] Sold under the trade name AH Mikhart 40 by Provencale S.A.
[2] Sold under the trade name Luviskol Plus by BASF
[4] Sold under the trade name Mirasil D-DML by Dow Corning
[5] Sold under the trade name Jeffsol Propylene Carbonate by Huntsman The aerosol device according to the invention which is used for packaging the above compositions comprises the following features:

a valve equipped with a nozzle and having an aperture size of 0.64 mm and an internal restriction aperture size of 0.64 mm, with an e additional gas intake of 0.64 mm;

a diffuser as described on the figures comprising three direct-outlet apertures of 0.5 mm in diameter for composition 1 and of 0.4 mm in diameter for composition 2.

The compositions were sprayed onto a body of hair. The spreading is fine and application is easy.

Following drying, the provision of volume and the bodying of the fibres is observed, while a natural appearance is retained.

The invention claimed is:

1. An aerosol device comprising:
   (a) a container comprising:
      at least one propellant; and
      a composition comprising:
         at least one fixing polymer, and/or
         at least one styling powder comprising at least one water-insoluble inorganic compound,
      wherein the at least one propellant is present in the container mixed with the composition or is present in the container separate from the composition; and
   (b) a diffuser disposed on the container and comprising:
      at least three spraying apertures for spraying a mixture of the at least one propellant and the composition in a spraying direction (Y), wherein axes of the at least three spraying apertures are parallel to each other and parallel to the spraying direction (Y);
      a delivery channel configured to receive the mixture from the container; and
      feed channels that are inclined obliquely relative to the spraying direction (Y) and the delivery channel, the feed channels being configured to respectively provide the mixture to the spraying apertures from the delivery channel.

2. The device according to claim 1, wherein the at least one fixing polymer is chosen from anionic, amphoteric, and nonionic fixing polymers.

3. The device according to claim 2, wherein the at least one anionic fixing polymer is selected from the group consisting of copolymers of acrylic and methacrylic acid or their salts, copolymers of crotonic acid, copolymers of monounsaturated C4-C8 carboxylic acids or anhydrides, polyacrylamides containing carboxylate groups, homopolymers or copolymers containing sulfonic groups, anionic polyurethanes, and anionic grafted silicone polymers.

4. The device according to claim 2, wherein the at least one nonionic polymer is chosen from polyalkyloxazolines; vinyl acetate homopolymers; vinyl acetate copolymers; homopolymers and copolymers of esters; copolymers of acrylonitrile and nonionic monomers; styrene homopolymers; styrene copolymers; polyamides; vinyl lactam homopolymers; vinyl lactam copolymers; non hydrolysed polyvinylformamide polymers; and polyvinyl alcohols.

5. The device according to claim 1, wherein the at least one propellant is present in the composition, and the at least one fixing polymer is present in an amount ranging from about 0.1% to about 20% by weight, relative to the total weight of the composition.

6. The device according to claim 1, wherein the at least one water-insoluble inorganic compound is selected from the group consisting of metal carbonates, oxides, sulfates, and silicates containing magnesium.

7. The device according to claim 1, wherein the at least one water-insoluble inorganic compound is selected from the group consisting of calcium carbonate, magnesium carbonate, alumina, barium sulfate, and magnesium oxide.

8. The device according to claim 1, wherein the composition is mixed with the at least one propellant, and the at least one water-insoluble inorganic compound is present in an amount ranging from about 0.1% to about 30% by weight, relative to the total weight of the composition.

9. The device according to claim 1, wherein the composition further comprises at least one C2-4 monoalcohol.

10. The device according to claim 9, wherein the at least one propellant is mixed with the composition, and the at least one C2-4 monoalcohol is present in an amount ranging from about 1% to about 70% by weight, relative to the total weight of the composition.

11. The device according to claim 1, wherein the composition further comprises at least one additive selected from the group consisting of anionic, cationic, nonionic, amphoteric and zwitterionic conditioning polymers, fragrances, dyes, UV-protective filters, acids, bases, nacres, and flakes.

12. The device according to claim 1, wherein the at least one propellant is selected from the group consisting of air, nitrogen, carbon dioxide, dimethyl ether, volatile hydrocarbons, chlorinated and/or fluorinated hydrocarbons, and mixtures thereof.

13. The device according to claim 1, wherein the at least one propellant is present in the composition in an amount ranging from about 10% to about 90% by weight, relative to the total weight of the composition.

14. The device according to claim 1, wherein the at least three spraying apertures are arranged at 120° from one another around the spraying direction.

15. The device according to claim 1, wherein the at least three spraying apertures are fixed on a single nozzle.

16. The device according to claim 1, wherein each of the at least three spraying apertures is connected to a feed duct, said feed duct inclined obliquely relative to the spraying direction.

17. A method for shaping and/or maintaining hair, comprising:
   (a) spraying a cosmetic composition from an aerosol device comprising:
      a container comprising:
         at least one propellant; and
         a composition comprising:
            at least one fixing polymer; and/or
            at least one styling powder comprising at least one water-insoluble inorganic compound;
         wherein the at least one propellant is present in the container mixed with the composition, or is present in the container separate from the composition; and a diffuser disposed on the container and comprising:
- at least three spraying apertures for spraying a mixture of the at least one propellant and the composition in a spraying direction (Y), wherein axes of the at least three spraying apertures are parallel to each other and parallel to the spraying direction (Y);
- a delivery channel configured to receive the mixture from the container; and
- feed channels that are inclined obliquely relative to the spraying direction (Y) and the delivery channel, the feed channels being configured to respectively provide the mixture to the at least three spraying apertures from the delivery channel; and (b) applying said composition to wet or dry hair; and (c) optionally, rinsing the hair after an optional leave-on time.

18. An aerosol device comprising:

(a) a container comprising:
- at least one propellant; and
- a composition comprising:
  - at least one fixing polymer, and/or
  - at least one styling powder comprising at least one water insoluble inorganic compound,
  - wherein the at least one propellant is present in the container mixed with the composition or is present in the container separate from the composition; and (b) a diffuser disposed on the container and comprising at least three spraying apertures for spraying a mixture of the at least one propellant and the composition in a spraying direction (Y) wherein axes of the at least three spraying apertures are parallel to each other and parallel to the spraying direction (Y);
- a delivery channel configured to receive the mixture from the container; and
- feed channels that are inclined obliquely relative to the spraying direction (Y) and the delivery channel, the feed channels being configured to respectively provide the mixture to the at least three spraying apertures from the delivery channel,
- wherein each spraying aperture comprises a first cylindrical section configured to receive the mixture from one of the feed channels, a conical section, and a second cylindrical section configured to expel the mixture from the diffuser, wherein the second cylindrical section has a smaller diameter than the first cylindrical section, wherein the conical section narrows and connects the first cylindrical section to the second cylindrical section, and
- wherein the delivery channel has a longitudinal axis that is inclined relative to a longitudinal axis (X) of the container.

19. A method for shaping and/or maintaining hair, comprising:

(a) spraying a cosmetic composition from an aerosol device comprising:
- a container comprising:
  - at least one propellant; and
  - a composition comprising:
    - at least one fixing polymer; and/or
    - at least one styling powder comprising at least one water insoluble inorganic compound;
  - wherein the at least one propellant is present in the container mixed with the composition or is present in the container separate from the composition; and
- a diffuser disposed on the container and comprising:
  - at least three spraying apertures for spraying a mixture of the at least one propellant and the composition in a spraying direction, wherein axes of each of the at least three spraying apertures are parallel to each other and parallel to a spraying direction (Y);
  - a delivery channel configured to receive the mixture from the container; and
  - feed channels that are inclined obliquely relative to the spraying direction (Y) and the delivery channel, the feed channels being configured to respectively provide the mixture to the at least three spraying apertures from the delivery channel;

(b) applying said composition to wet or dry hair; and (c) optionally, rinsing the hair after an optional leave-on time.

* * * * *